(12) United States Patent
Meurs

(10) Patent No.: US 8,334,096 B2
(45) Date of Patent: Dec. 18, 2012

(54) METHODS AND COMPOSITIONS RELATED TO ARRHYTHMOGENIC RIGHT VENTRICULAR CARDIOMYOPATHY (ARVC)

(75) Inventor: Kathryn M. Meurs, Viola, ID (US)

(73) Assignee: Washington State University Research Foundation, Pullman, WA (US)

( * ) Notice: Subject to any disclaimer, the term of this patent is extended or adjusted under 35 U.S.C. 154(b) by 283 days.

(21) Appl. No.: 12/799,574

(22) Filed: Apr. 26, 2010

(65) Prior Publication Data

US 2010/0273663 A1 Oct. 28, 2010

Related U.S. Application Data

(60) Provisional application No. 61/173,131, filed on Apr. 27, 2009.

(51) Int. Cl.
*C07H 21/04* (2006.01)
*C12Q 1/68* (2006.01)
(52) U.S. Cl. ............................ 435/6; 435/91.1; 435/91.2
(58) Field of Classification Search .................. None
See application file for complete search history.

(56) References Cited

PUBLICATIONS

Basso et al., "Arrhythmogenic right ventricular cardiomyopathy causing sudden cardiac death in boxer dogs: a new animal model of human disease," *Circulation*, 109(9): 1180-1185, 2004.

Baumwart et al., "Magnetic Resonance Imaging of Right Ventricular Morphology and Function in Boxer Dogs with Arrhythmogenic Right Ventricular Cardiomyopathy," *J. Vet. Intern. Med.*, 23: 271-274, 2009.

Cattanach, "Boxer Health Report to Boxer Breed Council," Posted Dec. 18, 2009 (3 pages). http://z13.invisionfree.com/Boxer_dog_rescue/index.php?showtopic=11934&view=getlastpost, Accessed Feb. 4, 2010.

Harpster, Boxer Cardiomyopathy, in Kirk R.W., ed., *Current Veterinary Therapy VIII Small Animal Practice*; 329-337, 1983.

Meurs et al., "Familial Ventricular Arrhythmias in Boxers," *J. Vet. Intern. Med.*, 13: 437-439, 1999.

Thiene et al., "Arrhythmogenic right ventricular cardiomyopathy/dysplasia," *Orphanet J. Rare Dis.*, 2(45): 1-16, 2007.

*Primary Examiner* — Nancy T Vogel
*Assistant Examiner* — Catherine Hibbert
(74) *Attorney, Agent, or Firm* — Klarquist Sparkman, LLP.

(57) ABSTRACT

This disclosure provides the identification of an eight base pair deletion in the 3'-untranslated region (UTR) of the striatin gene that is linked to arrhythmogenic right ventricular cardiomyopathy (ARVC) in Boxer dogs. Also provided are methods for detecting ARVC, methods of breeding Boxer dogs to reduce the prevalence or frequency of ARVC in a population, and methods of screening for a compound useful for treatment of ARVC.

11 Claims, 10 Drawing Sheets
(5 of 10 Drawing Sheet(s) Filed in Color)

Normal Dog

Heterozygous Dog

Homozygous dog

```
SEQUENCE LISTING

<160> NUMBER OF SEQ ID NOS: 4

<210> SEQ ID NO 1
<211> LENGTH: 65
<212> TYPE: DNA
<213> ORGANISM: Canis familiaris

<400> SEQUENCE: 1
gtgtgtgtgt gtgtgtgtat gcatgcgtac atacacacat acacacacac acacatatat    60
gaagt                                                                65

<210> SEQ ID NO 2
<211> LENGTH: 58
<212> TYPE: DNA
<213> ORGANISM: Canis familiaris

<400> SEQUENCE: 2
tgtgtgtgtg tgtgtgtgta tgcatgcgta catacacaca cacacacata tatgaagt      58

<210> SEQ ID NO 3
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 3
gcaacagcgc attctcactt tag                                            23

<210> SEQ ID NO 4
<211> LENGTH: 24
```

-continued

```
<212> TYPE: DNA
<213> ORGANISM: Artificial sequence
<220> FEATURE:
<223> OTHER INFORMATION: synthetic oligonucleotide

<400> SEQUENCE: 4
gtgggatggc tgatgactct attt                                          24
```

METHODS AND COMPOSITIONS RELATED TO ARRHYTHMOGENIC RIGHT VENTRICULAR CARDIOMYOPATHY (ARVC)

CROSS REFERENCE TO RELATED APPLICATION

This application claims priority to and the benefit of U.S. Provisional Application No. 61/173,131 filed Apr. 27, 2009, which is incorporated by reference herein in its entirety.

FIELD

This disclosure relates to methods and kits for detecting arrhythmogenic right ventricular cardiomyopathy (ARVC) based on the presence of a deletion in the striatin gene or a decrease in striatin gene expression, for instance particularly in dogs such as Boxer dogs. Further, it relates to methods of breeding Boxer dogs to decrease the prevalence of ARVC in a Boxer population.

BACKGROUND

The Boxer dog is the sixth (out of 156 registered dog breeds) most popular registered dog breed in the United States. Unfortunately the Boxer is also the most commonly reported breed to be affected with the cardiac disease, arrhythmogenic right ventricular cardiomyopathy (ARVC) (Basso et al., *Circulation*, 109:1180-1185, 2004). Previously termed Boxer cardiomyopathy, arrhythmogenic right ventricular cardiomyopathy in the Boxer dog is a familial disease that is inherited in an autosomal dominant pattern (Basso et al., *Circulation*, 109:1180-1185, 2004; Meurs et al., *J Vet Intern Med*, 13:437-439, 1999; Harpster, *Boxer Cardiomyopathy*, in Kirk R W, ed. *Current Veterinary Therapy VIII Small Animal Practice;* 329-337, 1983). Affected dogs suffer from rapid ventricular tachyarrhythmias that may lead to cardiac syncope or sudden cardiac death (FIG. 1). Postmortem evaluation includes the identification of unique histological fibrofatty replacement of myocardium in the right ventricle (and sometimes interventricular septum and left ventricle) (FIG. 2). The histopathological changes may lead to right, and sometimes left myocardial ventricular dysfunction. (Baumwart et al., *J Vet Intern Med*, 23:271-274, 2009).

Arrhythmogenic right ventricular cardiomyopathy is also a common cause of sudden cardiac death in human beings (Thiene et al., *Orphanet J Rare Dis.*, 2:45, 2007). The disease in human beings is most commonly a familial disease associated with a causative mutation in a gene that encodes for a desmosomal (cell junction) protein (Id).

At this time there is no single test that provides a definitive diagnosis of ARVC in the Boxer dog. Instead, the diagnosis is defined by a combination of the following findings: postmortem histological identification of fibrofatty replacement of myocardium in the right ventricle, ventricular tachyarrhythmias, syncope or exercise intolerance, and a history of familial disease (Basso et al., *Circulation*, 109:1180-1185, 2004; Harpster, *Boxer Cardiomyopathy*, in Kirk R W, ed. *Current Veterinary Therapy VIII Small Animal Practice;* 329-337, 1983). There is therefore a need to develop a test to definitively diagnose ARVC in Boxer dogs.

SUMMARY

Disclosed herein are methods of detecting arrhythmogenic right ventricular cardiomyopathy (ARVC) in a subject by detecting a defect in the striatin gene in the subject that results in reduced striatin expression. In some embodiments, detecting the defect in the striatin gene involves determining a reduction in striatin gene expression in comparison to a control. In other embodiments, detecting the defect involves detecting the deletion of an eight base pair sequence in the striatin 3'-untranslated region (UTR).

Also disclosed herein are methods of selectively breeding dogs to decrease the frequency of arrhythmogenic right ventricular cardiomyopathy (ARVC) in a dog population. The disclosed breeding methods involve identifying those dogs in a breeding population that have a predisposition to arrhythmogenic right ventricular cardiomyopathy (ARVC) by identifying a defect in the striatin gene that results in aberrant striatin expression; selecting for breeding those dogs that do not have a predisposition to ARVC; and breeding only selected dogs, thereby decreasing the frequency of ARVC in the dog population.

Additionally disclosed are methods of identifying a candidate compound for use in treating ARVC. These methods involve culturing cells from a Boxer dog with ARVC; measuring striatin gene expression in a population of the cultured cells to determine a control level of striatin expression; contacting a separate population of the cultured cells with a test compound; measuring striatin gene expression in the separate population after it is contacted with the test compound to determine a test level of striatin expression; comparing the control level of striatin expression with the test level of striatin expression; and selecting the test compound as a candidate for use in treating ARVC in a subject if the test level of striatin expression is greater than the control level of striatin expression.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawings will be provided by the Office upon request and payment of the necessary fee.

SEQUENCE LISTING

Figure 1:
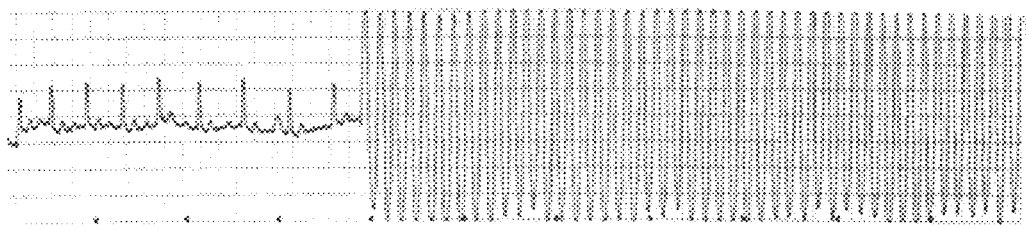
FIG. 1 is an electrocardiogram from a Boxer dog with ventricular tachyarrhythmia. The dog presented with a normal electrocardiogram (left side of figure) and then converted to a run of ventricular tachyarrhythmia (rapid cardiac complexes on the right side of strip) and fainted (syncope).
Figure 2:
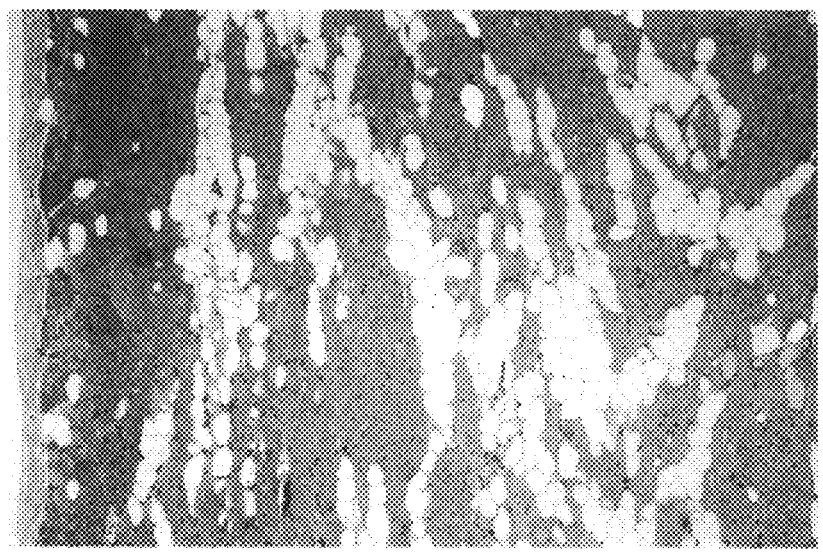
FIG. 2 shows a postmortem histological section taken from the heart of a Boxer dog affected by ARVC. Note the lipid infiltration and loss of cardiac tissue.

The nucleic and/or amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the nucleic acid sequence from the Boxer dog chromosome 17, positions 32,373,881-37,373,945. Nucleotides 38-45 of this sequence are deleted in ARVC-affected dogs.

SEQ ID NO: 2 is a nucleic acid sequence from the Boxer dog chromosome 17, beginning at position 32, 373, 880 from a dog that is homozygous for the eight base pair deletion in the striatin 3'-UTR. The junction of the deleted nucleotides is at nucleotides 37 and 38.

SEQ ID NOs 3 and 4 are the nucleic acid sequences for representative forward and reverse RT-PCT primers used to amplify striatin exon 1.

DETAILED DESCRIPTION

I. Abbreviations

AECG ambulatory electrocardiogram
ARVC arrhythmogenic right ventricular cardiomyopathy
ASOH allele-specific oligonucleotide hybridization
CCD charge-coupled device
cDNA complementary DNA
HPRT hypoxanthine-guanine phosphoribosyltransferase
IF immunofluorescence
Mb megabase
OLA oligonucleotide ligation assay
PCR polymerase chain reaction
PVDF polyvinylidene fluoride
RT-PCR reverse transcription polymerase chain reaction
UTR untranslated region
VPC ventricular premature contraction II Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Altered expression: Expression of a biological molecule (for example, mRNA or protein) in a subject or biological sample from a subject that deviates from expression of the same biological molecule in a subject or biological sample from a subject having normal or unaltered characteristics for the biological condition associated with the molecule. Aberrant expression is synonymous with altered expression. Normal expression can be found in a control, a standard for a population, etc. Altered or aberrant expression of a biological molecule may be associated with a disease. The term "associated with" includes an increased risk of developing the disease as well as the disease itself. Expression may be altered in such a manner as to be increased or decreased. The directed alteration in expression of mRNA or protein may be associated with therapeutic benefits. In particular examples, altered expression of a gene, for example striatin, is a result of a defect in that gene.

Altered protein expression refers to expression of a protein that is in some manner different from expression of the protein in a normal (wild type) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of an decreased amount of the protein, compared to a control or standard amount; (6)

alteration of the subcellular localization or targeting of the protein; (7) alteration of the temporally regulated expression of the protein (such that the protein is expressed when it normally would not be, or alternatively is not expressed when it normally would be); and (8) alteration of the localized (for example, organ or tissue specific) expression of the protein (such that the protein is not expressed where it would normally be expressed or is expressed where it normally would not be expressed), each compared to a control or standard.

Amplify: Increase the number or amount of a compound. To amplify a molecule or sequence of DNA is to increase the copy number of the particular DNA molecule or sequence, e.g., through an in vitro amplification technique. DNA can be amplified by any method that replicates the DNA sequence and increases the copy number of that sequence. In particular examples, DNA amplification is achieved in some embodiments using a PCR-based method including RT-PCR. Other exemplary methods of DNA amplification include isothermal amplification methods. Other representative and non-limiting examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science,* 242:423-426, 1988; Huston et al., *Proc. Natl. Acad. Sci.,* 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.,* 90:6444-6448, 1993; Poljak et al., *Structure,* 2:1121-1123, 1994). A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

ARVC (arrhythmogenic right ventricular cardiomyopathy): a familial cardiac disease that is inherited in an autosomal dominant pattern. Affected dogs suffer from rapid ventricular tachyarrhythmias that may lead to cardiac syncope or sudden cardiac death. Histopathology of cardiac tissue from ARVC-affected dogs shows fibrofatty replacement of myocardium in the right ventricle (and sometimes interventricular septum and left ventricle). ARVC is commonly diagnosed through: post-mortem histological identification of fibrofatty replacement of myocardium in the right ventricle, ventricular tachyarrhythmias, syncope or exercise intolerance and a history of familial disease. ARVC was previously known as Boxer cardiomyopathy.

Boxer dog: A breed of domesticated short hair dogs; part of the Molosser group of dog breeds. The Boxer dog is known for its characteristic short, stocky shape, though the head is the most distinctive feature of the Boxer.

Breeding population: A population of dogs who are potentially suitable for breeding (producing successive generations of dogs). A breeding population can be of any number of dogs, though it must include at least one male and one female dog.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

Contacting: "Contacting" includes in solution and solid phase, for example contacting cells or other biological sample with a test compound. In one example, contacting includes contacting a population of cells isolated from an ARVC-affected dog.

Control: A "control" refers to a sample or standard used for comparison with a test sample. In some embodiments, the control is a sample obtained from a healthy subject that does not have symptoms of or a predisposition to a disease such as ARVC. In some embodiments, the control is a historical control or standard reference value or range of values (such as a previously tested control sample, such as a group of ARVC-unaffected subjects, or group of samples that represent baseline or normal values, such as the normal level of striatin RNA or protein expression in an ARVC-unaffected subject). Control standards and values may be set based on a known or determined population value and may be supplied in the format of a graph or table that permits easy comparison of measured, experimentally determined values.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. The determination of a given order of nucleotides in a DNA of interest is referred to as DNA sequencing.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Deletion: The removal of a sequence of DNA (which may be as short as a single nucleotide), the regions on either side being joined together. A deletion in a DNA sequence is a genetic defect that can be directly detected by sequencing the region of DNA encompassing the site of deletion, thereby detecting the absence of the particular deleted sequence.

Frequency: A measure of the incidence of a disease in a population. Disease frequency is determined by any method known to the art of diagnosing the particular disease in the population. In particular examples, the frequency of ARVC in a dog population can be determined by detecting the herein-described eight base pair deletion in the striatin 3'-UTR.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a subject to an agent that inhibits gene expression. Expression of a gene also may be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression may be measured at the RNA level or the protein level and by any method known in the art, including Northern blot, RT-PCR, primer extension, Western blot, immunofluorescent or immunocytochemical protein detection, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation, includes but is not necessarily limited to overexpression, underexpression, or suppression of expression. In addition, it is understood that modulation of nucleic acid expression may be associated with, and in fact may result in, a modulation in the expression of an encoded protein or even a protein that is not encoded by that nucleic acid.

Expression of a target gene may be measured by any method known to those of skill in the art, including for example measuring mRNA or protein levels. It is understood that a measurable reduction in gene expression is relative, and does not require absolute suppression of the gene. A measurable reduction in gene expression is a test sample only requires that gene expression is measurably less than a control. Thus, in certain embodiments, a measurable reduction in gene expression requires that the gene is expressed at least 5% less than control expression levels, or at least 10% less, at least 15% less, at least 20% less, at least 25% less, or even more reduced from control levels. Thus, in some particular embodiments, a measurable reduction in gene expression is about 30%, about 40%, about 50%, about 60%, or more reduced from control levels. In specific examples, expression is reduced by 70%, 80%, 85%, 90%, 95%, or even more. Gene expression is substantially eliminated when expression of the gene is reduced by 90%, 95%, 98%, 99% or even 100%.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between to distinct nucleic acid sequences or two distinct regions of the same nucleic acid sequence.

Isolated: An isolated biological component (such as a nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been isolated thus include nucleic acids and proteins purified by standard purification methods. The term also embraces nucleic acids, peptides and proteins prepared by recombinant expression in a host cell as well as chemically synthesized nucleic acids. The terms isolated and purified do not require absolute purity; rather, it is intended as a relative term. Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

Mutation: Any change of DNA sequence, for instance within a gene or chromosome. As used herein, the term "genetic defect" is synonymous with "mutation". In some instances, a mutation will alter a characteristic or trait (phenotype), but this is not always the case. Types of mutations include base substitution point mutations (for example, transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term also encompasses DNA alterations that are present constitutionally, that alter the function of the encoded protein in a readily demonstrable manner, and that can be inherited by the children of an affected individual.

Gene mutations that occur outside of amino acid coding regions (i.e. untranslated regions) may also affect gene expression by alerting the binding sites for transcription factors on the DNA.

Nucleic acid molecule: A polymeric form of nucleotides, which may include both sense and anti-sense strands of ribonucleic acid (RNA), cDNA, genomic DNA, and synthetic forms and mixed polymers thereof A nucleotide refers to a ribonucleotide, deoxynucleotide or a modified form of either type of nucleotide. A nucleic acid molecule as used herein is synonymous with nucleic acid and polynucleotide. A nucleic acid molecule is usually at least 10 bases in length, unless otherwise specified. The term includes single- and double-stranded forms. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, the left hand end of a polynucleotide sequence written in the sense orientation is the 5' end and the right hand end of the sequence is the 3' end. In addition, the left hand direction of a polynucleotide sequence written in the sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules and morpholinos.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Polymerase Chain Reaction (PCR): An in vitro amplification technique that increases the number of copies of a nucleic acid molecule (for example, a nucleic acid molecule in a sample or specimen). The product of a PCR can be characterized by standard techniques known in the art, such as electrophoresis, restriction endonuclease cleavage patterns, oligonucleotide hybridization or ligation, and/or nucleic acid sequencing.

In some examples, PCR utilizes primers, for example, DNA oligonucleotides 10-100 nucleotides in length, such as about 15, 20, 25, 30 or 50 nucleotides or more in length (such as primers that can be annealed to a complementary target DNA strand by nucleic acid hybridization to form a hybrid between the primer and the target DNA strand). Primers can be selected that include at least 15, at least 20, at least 25, at least 30, at least 35, at least 40, at least 45, at least 50 or more consecutive nucleotides of a cancer survival factor-associated nucleotide sequence.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990).

Predisposition to a disease: To be susceptible and prone to a disease. A genetic defect that results in (or causes) a disease can make a subject "predisposed" to the particular disease, though the subject may not yet exhibit physical symptoms of the disease. Such a subject may become symptomatic over time or upon exposure to certain environmental or other stimulus. In particular examples, dogs carrying a genetic defect in the 3'-UTR of the gene encoding striatin (as described herein) that do not show symptoms of ARVC (e.g., prior to adulthood) can be considered to be predisposed to ARVC prior to symptom presentation.

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates a sign or symptom of a disease or pathological condition after it has begun to develop.

Protein: A biological molecule, particularly a polypeptide, expressed by a gene and comprised of amino acids.

Purified: In a more pure form than is found in nature. The term purified does not require absolute purity; rather, it is intended as a relative term. Thus, for example, a purified protein preparation is one in which the protein referred to is more pure than the protein in its natural environment within a cell.

The term substantially purified as used herein refers to a molecule (for example, a nucleic acid, polypeptide, oligonucleotide, etc.) that is substantially free of other proteins, lipids, carbohydrates, or other materials with which it is naturally associated. In one embodiment, a substantially purified molecule is a polypeptide that is at least 50% free of other proteins, lipids, carbohydrates, or other materials with which it is naturally associated. In another embodiment, the polypeptide is at least at least 80% free of other proteins, lipids, carbohydrates, or other materials with which it is naturally associated. In yet other embodiments, the polypeptide is at least 90% or at least 95% free of other proteins, lipids, carbohydrates, or other materials with which it is naturally associated.

Quantitative real time PCR: A method for detecting and measuring products generated during each cycle of a PCR, which products are proportionate to the amount of template nucleic acid present prior to the start of PCR. The information obtained, such as an amplification curve, can be used to quantitate the initial amounts of template nucleic acid sequence.

Reverse-transcription PCR(RT-PCR): A method for detecting, quantifying, or utilizing RNA present in a sample by a procedure wherein the RNA serves as a template for the synthesis of cDNA by a reverse transcriptase followed by PCR to amplify the cDNA. RT-PCR can be used in combination with quantitative real time PCR as a method of measuring the quantity of starting template in the reaction.

RNA (ribonucleic acid): A typically linear polymer of ribonucleic acid monomers, linked by phosphodiester bonds. Naturally occurring RNA molecules fall into three general classes, messenger (mRNA, which encodes proteins), ribosomal (rRNA, components of ribosomes), and transfer (tRNA, molecules responsible for transferring amino acid monomers to the ribosome during protein synthesis). Messenger RNA includes heteronuclear (hnRNA) and membrane-associated polysomal RNA (attached to the rough endoplasmic reticulum). Total RNA refers to a heterogeneous mixture of all types of RNA molecules.

Sample (or biological sample): A biological specimen containing genomic DNA, RNA (including mRNA), protein, or combinations thereof, obtained from a subject. Examples include, but are not limited to, peripheral blood or a fraction thereof, fine needle aspirate, urine, saliva, cheek swab, tissue biopsy, surgical specimen, and autopsy material.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS USA*, 85:2444, 1988); Higgins and Sharp (*Gene*, 73:237-244, 1988); Higgins and Sharp (*CABIOS* 5:151-153, 1989); Corpet et al. (*Nuc. Acids Res.* 16:10881-10890, 1988); Huang et al. (*Comp. Appls Biosci.* 8:155-165, 1992); and Pearson et al. (*Meth. Mol. Biol.* 24:307-31, 1994). Altschul et al. (*Nature Genet.*, 6:119-129, 1994) presents a detailed consideration of sequence alignment methods and homology calculations.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology Part I, Ch.* 2, Elsevier, New York, 1993).

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference. The following is an exemplary set of hybridization conditions:

Very High Stringency (Detects Sequences that Share 90% Identity)

| | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

High Stringency (Detects Sequences that Share 80% Identity or Greater)

| | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

Low Stringency (Detects Sequences that Share Greater than 50% Identity)

| | |
|---|---|
| Hybridization: | 6x SSC at RT to 55° C. for 16-20 hours |
| Wash at least twice: | 2x-3x SSC at RT to 55° C. for 20-30 minutes each. |

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specifically hybridizable and specifically complementary are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Striatin gene: A gene encoding the striatin protein, a known neuronal protein; shown herein to be desmosomal and expressed in cardiac tissue. Striatin is also known as calmodulin binding protein. The sequence of the full-length striatin gene on the dog chromosome 17 is available online at the UCSC genome browser at genome.ucsc.edu/cgi-bin/hgTracks?position=chr17:32375918-32435652&hgsid=157693646&xenoRefGene=pack&hgFind.matches=NM_003162. This sequence is also available online at the Ensembl genome browser at uswest.ensembl.org/Canis_familiaris/Gene/Summary?g=ENSCAFG00000005936.

Subject: Living multi-cellular vertebrate organism, a category that includes human and non-human mammals. In particular examples, the subject is a canine subject. In other examples, the canine subject is a particular breed of dog, such as a Boxer dog.

Therapeutic: A generic term that includes both diagnosis and treatment.

Therapeutically effective amount: A quantity of compound sufficient to achieve a desired effect in a subject being treated.

An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Treating a disease: Includes inhibiting or preventing the partial or full development or progression of a disease, for example in an animal or person who is known to have a predisposition to a disease. Furthermore, treating a disease refers to a therapeutic intervention that ameliorates at least one sign or symptom of a disease or pathological condition, or interferes with a pathophysiological process, after the disease or pathological condition has begun to develop.

Under conditions sufficient for: A phrase that is used to describe any environment that permits the desired activity.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein are methods of detecting arrhythmogenic right ventricular cardiomyopathy (ARVC) in a subject comprising detecting a defect in the striatin gene in a subject, wherein the defect results in reduced striatin expression. In some examples, the subject is canine. In other examples, the canine subject is a Boxer dog. In particular examples, detecting a defect in the striatin gene comprises measuring striatin gene expression in a test sample from the subject; and comparing the striatin gene expression in the test sample to a control; wherein measurably less striatin expression in the test sample in comparison to the control indicates that the subject has arrhythmogenic right ventricular cardiomyopathy (ARVC). In some examples, striatin gene expression is determined by measuring striatin RNA in the test sample. In other examples striatin gene expression is determined by measuring striatin protein in the test sample. In still other examples the control is a standard reference value.

In still other examples, detecting a defect in the striatin gene comprises detecting a deletion of an eight base pair sequence of the 3'-untranslated region (UTR) of the striatin gene, wherein the eight base pair sequence corresponds to nucleotides 38-45 of SEQ ID NO: 1. In some examples, detecting the deletion of an eight base pair sequence of the 3'-untranslated region (UTR) of the striatin gene comprises isolating DNA from the subject; and sequencing a region of the DNA including the nucleotide sequence corresponding to nucleotides 38-45 of SEQ ID NO: 1. Other examples involve amplifying the region of the DNA including the nucleotide sequence corresponding to nucleotides 38-45 of SEQ ID NO: 1 before sequencing the region of the DNA.

Also provided herein are methods of selectively breeding dogs to decrease the frequency of arrhythmogenic right ventricular cardiomyopathy (ARVC) in a dog population comprising identifying dogs in a breeding population, for example a Boxer dog population, that have a predisposition to arrhythmogenic right ventricular cardiomyopathy (ARVC) identifying a defect in the striatin gene, wherein the defect results in aberrant striatin expression; selecting for breeding those dogs that do not have a predisposition to arrhythmogenic right ventricular cardiomyopathy (ARVC); and breeding only selected dogs, thereby decreasing the frequency of arrhythmogenic right ventricular cardiomyopathy in the dog population.

In particular examples, detecting a defect in the striatin gene comprises measuring striatin gene expression in test samples from the dogs in the breeding population; and comparing the striatin gene expression in the test samples with a control. In some examples, measuring striatin gene expression comprises measuring striatin RNA in the test samples. In other examples, measuring striatin gene expression comprises measuring striatin protein in the test samples. In particular examples, the control is a standard reference value.

In still other examples, detecting a defect in the striatin gene comprises detecting a deletion of an eight base pair sequence of the 3'-untranslated region (UTR) of the striatin gene, wherein the eight base pair sequence corresponds to nucleotides 38-45 of SEQ ID NO: 1. In some examples, detecting the deletion of an eight base pair sequence of the 3'-untranslated region (UTR) of the striatin gene comprises isolating DNA from the dogs of the population; and sequencing a region of the DNA including the nucleotide sequence corresponding to nucleotides 38-45 of SEQ ID NO: 1. In other examples, the region of the DNA encompassing the nucleotide sequence corresponding to nucleotides 38-45 of SEQ ID NO: 1 is amplified prior to sequencing the region of the DNA.

Also provided herein are methods of identifying a candidate compound for use in treating arrhythmogenic right ventricular cardiomyopathy (ARVC) in a subject, comprising culturing cells from a Boxer dog with arrhythmogenic right ventricular cardiomyopathy (ARVC); measuring striatin gene expression in a population of the cultured cells to determine a control level of striatin expression; contacting a separate population of the cultured cells with a test compound; measuring striatin gene expression in the separate population after it is contacted with the test compound to determine a test level of striatin expression; comparing the control level of striatin expression with the test level of striatin expression; and selecting the test compound as a candidate for use in treating arrhythmogenic right ventricular cardiomyopathy (ARVC) in a subject if the test level of striatin expression is greater than the control level of striatin expression.

IV. ARVC and its Diagnosis

Arrhythmogenic right ventricular cardiomyopathy (ARVC) is an autosomal dominant cardiac disease of Boxer dogs. Though inherited, ARVC symptoms are adult-onset. Thus, as with many genetic disorders, prior to the onset of symptoms, subjects carrying a causative genetic defect can be considered "predisposed" to the disease. ARVC-affected dogs suffer from rapid ventricular tachyarrhythmias that may lead to cardiac syncope or sudden cardiac death. Postmortem evaluation from affected dogs has shown that loss of normal cardiac function correlates with unique histological fibrofatty replacement of myocardium in the right ventricle (and sometimes interventricular septum and left ventricle). Prior to this disclosure, ARVC diagnosis relied upon the detection of observable cardiac dysfunction combined with available family history of ARVC.

Figure 4A:
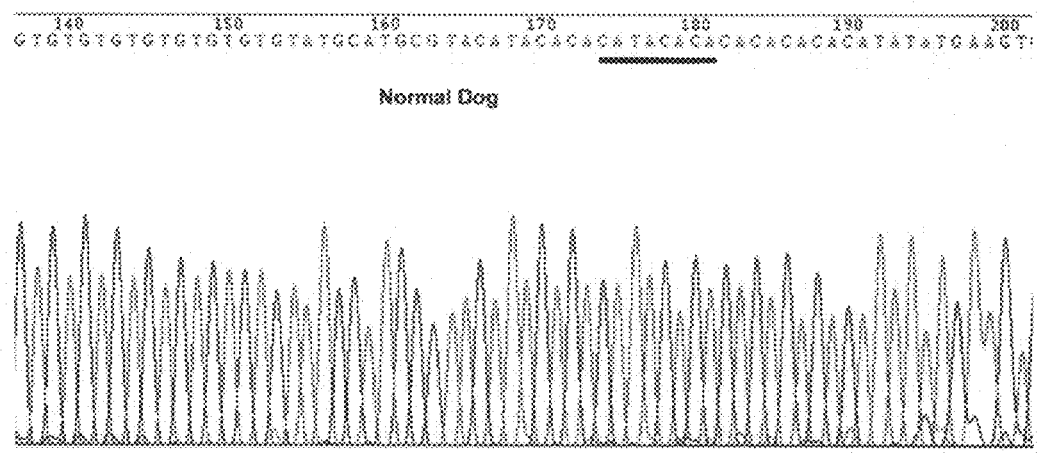
FIG. 4 are three DNA sequence chromatograms showing the identification of an eight base pair deletion in a 3' untranslated region of the canine striatin gene in affected ARVC Boxers. A) Sequence from a dog not affected by ARVC. The underlined region is deleted in affected dogs. B) Sequence from an ARVC-affected dog with one copy of the deletion (heterozygous) and one copy of the sequence present (underlined) The chromatograms of the different alleles present in the heterozygote diverge following the deletion. Sequence divergence due to the deletion is also shown by the machine-assignment of the variable "N" at positions where the automated sequencer was unable to distinguish between peaks in the diverged sequences. C) Sequence from an ARVC-affected with both copies deleted (homozygous). Underlined area from FIG. 4A is missing.
Figure 4B:
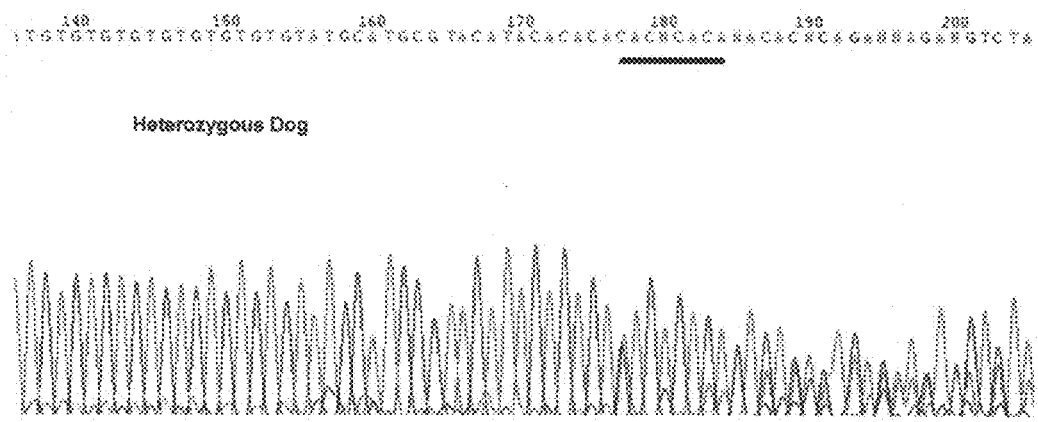

Disclosed herein is the unexpected finding that ARVC results from a genetic defect in the striatin gene. The genetic defect is an eight base pair deletion in the 3' untranslated region (UTR) of the striatin gene. The sequence that is deleted, which is underlined in FIG. 4A, occurs on the Boxer dog chromosome 17 between base pairs 32,373,918 and 32,373,925, and corresponds to positions 38-45 of SEQ ID NO: 1. The sequence of a portion of the striatin 3'-UTR from a homozygous mutant ARVC-affected dog is shown in SEQ ID NO: 2. As shown in FIG. 4, this deletion is specific to ARVC-affected Boxer dogs. It was not observed in either unaffected Boxers.

To date, this mutation has not been observed in dogs of eleven other breeds examined. However, given that this is a small fraction of known dog breeds (less than 10%), one of skill in the art will appreciate that the absence of this eight base pair sequence may be a feature of other ARVC-affected dogs breeds. Moreover, with the appreciation of the effect of this deletion on striatin expression and its association with ARVC, it will now be recognized that a defect in the striatin gene that perturbs striatin expression may be a hallmark of ARVC in other species.

Though previously identified as a neuronally-expressed protein, striatin was not known to be expressed in cardiac tissue until the studies reported herein. Also disclosed herein is the observation that striatin is a desmosomal protein. As shown herein, the eight base pair deletion in the striatin 3'-UTR results in a measurable reduction in striatin gene expression in the cardiac tissue of ARVC-affected dogs.

V. Molecular Methods of Diagnosing ARVC

The determination that ARVC in Boxer dogs is caused by a measurable reduction in striatin expression resulting from an eight base pair deletion in the striatin 3'-UTR allows for molecular methods of ARVC diagnosis that are not reliant on ARVC symptom onset. The deleted sequence (CATACACA), which is also shown in FIG. 4A (as indicated by the black bar), occurs on chromosome 17 between base pairs 32,373,918 and 32,373,925, and corresponds to positions 38-45 of SEQ ID NO: 1. For reference, the entire sequence of canine Chromosome 17 is incorporated herein by reference based on the publicly available Boxer dog sequence from GenBank (e.g., NW_876263; NW_876263.1) as of Apr. 27, 2009. Boxer dog genomic sequence can also be viewed at the USCS Genome Bioinformatics site, available on-line at genome.ucsc.edu/cgi-bin/hgGateway?org=Dog&db=canFam2&hgsid=156525325.

From the current disclosure, it will be appreciated that the genetic defect in the striatin gene is detectable by any method of one or both of a) detecting the ARVC-specific eight base pair deletion in the striatin 3'-UTR or b) detecting a measurable reduction in striatin gene expression; and it will be further appreciated that detection of the genetic defect is a suitable diagnostic test for ARVC in a Boxer dog. Moreover, it will also be understood that diagnosis of ARVC in a Boxer dog enables proactive treatment of the affected dog for instance with pharmaceutical agent(s) that minimize the cardiac dysfunction. Additionally, information regarding a Boxer dog's ARVC status (unaffected, homozygous, or heterozygous) as indicated by the described deletion in the striatin 3-UTR (or by measurable reduction in striatin gene expression) can for instance be tested early in the life of the individual, and included on a license, medical record, pedigree, and so forth. Optionally, such information can be used in making breeding decisions with regard to the tested individual.

As noted above, ARVC in humans has also been associated with a mutation in a desmosomal protein expressed in myocardial tissue. Thus, it will be appreciated from the teachings herein that the identified deletion in the 3'-UTR of striatin (a desmosomal protein) in Boxers will be useful for studying and/or identifying ARVC in other dog breeds, and other animals (including humans).

A. Detection of a Deletion of a Sequence in the Striatin 3'-UTR

In one embodiment of the disclosed methods, ARVC-affected Boxer dogs are identified by the detection of the deletion of an eight base pair sequence in the striatin 3'-UTR. The eight base pairs that are absent in ARVC affected Boxer dogs are described herein as nucleotides 38-45 of SEQ ID NO: 1. To perform a diagnostic test for the presence or absence of this eight base pair sequence, a suitable genomic DNA-containing sample from a subject is obtained and the DNA extracted using conventional techniques. DNA is extracted from any suitable tissue sample, for example, a blood sample, a buccal swab, a hair follicle preparation, or a nasal aspirate is used as a source of cells to provide the DNA sample. In a particular embodiment, the extracted DNA is then subjected to amplification, for example according to standard procedures. The presence or absence of the eight base pair striatin 3'-UTR sequence is determined by sequencing a region of DNA encompassing the chromosomal location of the eight base pair deletion using conventional DNA sequencing methods including manual and automated fluorescent DNA sequencing, primer extension methods (Nikiforov et al., *Nucl. Acids Res.* 22:4167-4175, 1994), allele-specific PCR methods (Rust et al., *Nucl. Acids Res.* 6:3623-3629, 1993), RNase mismatch cleavage, single-strand conformation polymorphism (SSCP), denaturing gradient gel electrophoresis (DGGE), oligonucleotide hybridization, and the like. Also, see the following U.S. patents for descriptions of methods or applications of polymorphism analysis to disease prediction and/or diagnosis: U.S. Pat. Nos. 4,666,828; 4,801,531; 5,110,920; 5,268,267; and 5,387,506.

In some embodiments, sequences surrounding and overlapping the eight base pair striatin gene deletion, such as sequences comprising SEQ ID NO: 1, can be useful for a number of gene mapping, targeting, and detection procedures. For example, genetic probes can be readily prepared for hybridization and detection of the described deletion. Such probe sequences may be greater than about 12 or more oligonucleotides in length and possess sufficient complementarity to distinguish between a wild-type and an eight base pair deletion sequence. Similarly, sequences surrounding and overlapping the specifically disclosed deletion can be utilized in allele-specific hybridization procedures.

In some embodiments, the deletion of the eight base pair sequence in the striatin 3'-UTR (for example, nucleotides 38-45 of SEQ ID NO: 1) can be detected by allele-specific oligonucleotide hybridization (ASOH) (Stoneking et al., *Am. J. Hum. Genet.* 48:370-382, 1991), which involves hybridization of labeled oligonucleotide probes to the sequence, stringent washing, and signal detection. In other embodiments, applicable methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

The absence of the eight base pair sequence in the striatin 3'-UTR (that is, the "presence" of the deletion) can also be detected by dynamic allele-specific hybridization (DASH), which involves dynamic heating and coincident monitoring of DNA denaturation, as disclosed by Howell et al. (*Nat. Biotech.* 17:87-88, 1999). A target sequence is amplified (e.g., by PCR) using one biotinylated primer. The biotinylated product strand is bound to a streptavidin-coated microtiter plate well (or other suitable surface), and the non-biotinylated strand is rinsed away with alkali wash solution. An oligonucleotide probe, specific for one allele (e.g., the wild-type allele), is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect the eight base pair deletion in the canine DNA. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods.

B. Detection of a Measurable Reduction in Striatin Gene Expression

In another embodiment of the disclosed methods, ARVC-affected Boxer dogs (or other subjects) are identified by detecting measurably less striatin gene expression in cardiac tissue of the subject (e.g., ARVC-affected dog) in comparison to a control.

In particular examples, the control is the level of striatin expression in a sample obtained from at least one healthy subject that does not have symptoms of or a predisposition to ARVC. In other examples, the control is a historical control or standard reference value or range of values (such as a previously tested control sample, for instance the average or otherwise collective level of a group of ARVC-unaffected subjects, or group of samples that represent baseline or normal values, such as the normal level of striatin RNA or protein expression in an ARVC-unaffected subject of the same breed or species). Control standards and values may be set based on a known or determined population value and may be supplied, for instance, in the form of a graph or table that permits easy comparison of measured, experimentally determined values.

Gene expression can be measured by any method known to the art and includes measurements taken at either or both the level of transcription (level of striatin RNA) or translation (level of striatin protein). The determination that a given Boxer dog has a measurably less striatin gene expression than a control indicates that the dog is predisposed to or affected by ARVC.

In particular embodiments where transcription is measured, RT-PCR or quantitative real time RT-PCR is used to measure striatin expression. In other embodiments, quantitative primer extension is used. In still other embodiments Northern blotting is used to measure striatin expression.

Methods of gene expression profiling include methods based on hybridization analysis of polynucleotides, methods based on sequencing of polynucleotides, and proteomics-based methods. In some examples, mRNA expression in a sample is quantified using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, in normal and tumor tissues, with or without drug treatment, to characterize patterns of gene expression, to discriminate between closely related mRNAs, and to analyze RNA structure.

Methods for quantitating mRNA are well known in the art. In some examples, the method utilizes RT-PCR. For example, extracted RNA can be reverse-transcribed using a Gene-Amp® RNA PCR kit (Perkin Elmer, Calif., USA), following the manufacturer's instructions.

For example, TaqMan® RT-PCR can be performed using commercially available equipment. The system can include a thermocycler, laser, charge-coupled device (CCD) camera, and computer. The system amplifies samples in a 96-well format on a thermocycler. During amplification, laser-induced fluorescent signal is collected in real-time through fiber optic cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes HPRT, GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems (Foster City, Calif.).

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some examples, gene expression is identified or confirmed using a microarray-based technique. For instance, the expression profile can be measured in either fresh or paraffin-embedded tissue, using microarray technology. In another example of an array-based method, one or more striatin nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest.

In other embodiments, translation of striatin is used to determine if there is a measurable reduction in striatin expression. In such embodiments, striatin translation can be measured quantitatively (e.g. by quantitative Western blot) or qualitatively (immunofluorescent or immunohistochemical labeling of striatin protein in a section of cardiac tissue). Therefore, antibodies specific for striatin can be used to routinely detect a measurable reduction in striatin expression. Such evaluations can be performed, for example, in lysates prepared from cells, in fresh or frozen cells, in cells that have been smeared or touched on glass slides and then either fixed and/or dried, or in cells that have been fixed, embedded (e.g., in paraffin), and then prepared as histological sections on glass slides.

Localization and/or coordination of striatin expression (temporally or spatially) can also be examined using known techniques, such as isolation and comparison of striatin from subcellular fractions, including specific organelles, or from specific cell or tissue types, or at specific time points after an experimental manipulation. Demonstration of reduced striatin protein levels, in comparison to such expression in a control cell (e.g., normal, as in taken from a subject not affected by ARVC) or other standard, would be an alternative or supplemental approach to the direct determination of the status of the striatin 3'-UTR by the methods outlined above and equivalents.

The availability of antibodies specific to the striatin protein will facilitate the detection and quantitation of cellular striatin by one of a number of immunoassay methods which are well known in the art and are presented in Harlow and Lane (*Antibodies, A Laboratory Manual*, CSHL, New York, 1988). Any standard immunoassay format (e.g., ELISA, western blot, or RIA assay) can be used to measure striatin polypeptide or protein levels, and to compare these with striatin expression levels in control, reference, cell populations.

By way of example, an ELISA is one type of immunoassay that can be used to determine the concentration of striatin in a sample from subject. A typical ELISA format involves a specific immobilized capture antibody, sample, a labeled detection antibody, chromogens, and stop solution. Antigen will bind to the immobilized capture antibody and thus can be detected with one or more antibodies. The antibody detection technique used with an ELISA may be direct or indirect. For direct antibody visualization of the striatin protein, anti-striatin antibody is attached to a substrate, the substrate is incubated with a sample, and the substrate is then incubated with another anti-striatin antibody that has been enzyme-conjugated, for example an anti-striatin antibody conjugated to alkaline phosphatase or horseradish peroxidase. For indirect antibody visualization of the striatin protein, anti-striatin antibody is attached to the substrate, and the substrate is incubated with a sample. The substrate is then incubated with an unconjugated striatin-specific antibody (primary antibody), then with an enzyme-conjugated antibody (secondary antibody) that recognizes the primary antibody. Secondary antibodies for the indirect detection of primary antibodies are often conjugated with horseradish peroxidase or alkaline phosphatase. A substrate solution is then added, acted upon by the enzyme, and effects a color change. The intensity of the color change is proportional to the amount of antigen in the original sample. Primary and secondary antibodies also can be coupled to radioactive or fluorescent tags. The intensity of radioactive or fluorescent labeling is proportional to the amount of antigen present in the original sample.

In an alternative embodiment, striatin can be assayed in a sample by a competition immunoassay, such as a radioimmunoassay (RIA) utilizing striatin standards labeled with a detectable substance, such as radiolabel, and an unlabeled antibody that specifically binds striatin. In this assay, the labeled striatin standard is mixed with the striatin-reactive antibody. Then, the sample is combined with the antibody-bound labeled striatin standards. The amount of unbound, labeled striatin is then determined. The amount of striatin in the sample is proportional to the amount of unbound, labeled striatin.

Immunohistochemical or immunofluorescence techniques may also be utilized for striatin polypeptide or protein detection. For example, a tissue sample may be obtained from a subject, and a section stained for the presence of striatin using a striatin specific binding agent (e.g., anti-striatin antibody) and any standard detection system (e.g., one which includes a secondary antibody conjugated to horseradish peroxidase or fluorescent label). General guidance regarding such techniques can be found in, e.g., Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating a striatin protein, a biological sample of the subject, which sample includes cellular proteins, is required. Such a biological sample may be obtained from body cells, such as those present in a tissue biopsy, surgical specimens, or autopsy material.

Figure 5:
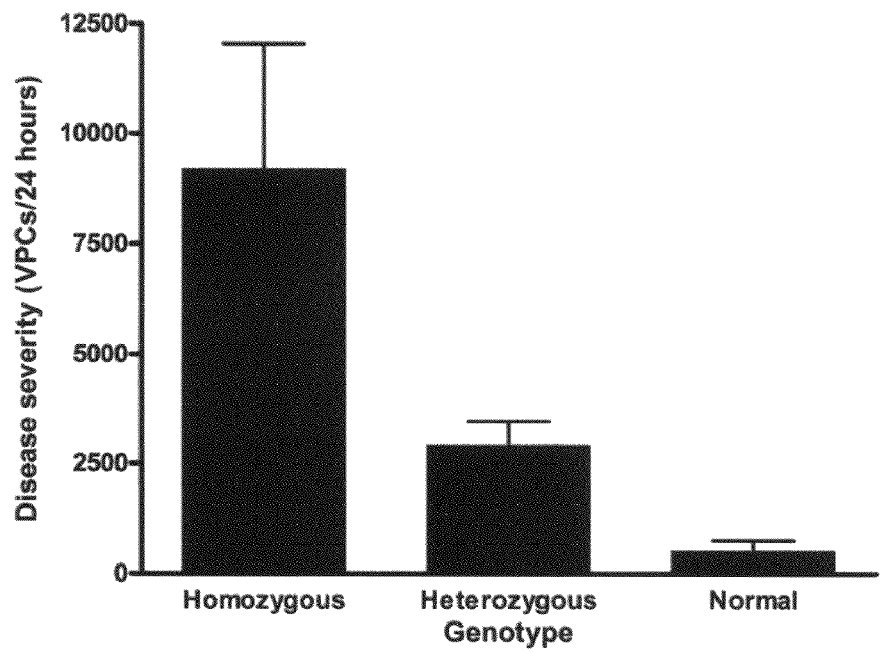
FIG. 5 is a graph showing that homozygous dogs affected by ARVC had a statistically greater number of ventricular premature contractions/24 hours and therefore, more severe disease than heterozygous dogs (4281 and 1385, respectively) ($p<0.05$).

VI. Differentiation of Individuals Homozygous Versus Heterozygous for Striatin 3'-UTR Deletion As shown in FIG. 5, ARVC severity depends on whether a subject is homozygous or heterozygous for the deletion in the striatin 3'-UTR. Thus, it may sometimes be beneficial to determine whether a subject is homozygous or heterozygous for the mutation. For instance, a homozygous individual may warrant a more urgent (rapid) or more severe treatment regimen than a heterozygous individual.

By way of example, the oligonucleotide ligation assay (OLA), as described at Nickerson et al. (*Proc. Natl. Acad. Sci. USA* 87:8923-8927, 1990), allows the differentiation between individuals who are homozygous versus heterozygous for the deletion in the striatin 3'-UTR. As an example of the OLA assay, when carried out in microtiter plates, one well is used for the determination of the presence of the striatin allele that contains the eight base pair deletion in the 3'-UTR and a second well is used for the determination of the presence of the wild type striatin 3'-UTR sequence. Thus, the results for an individual who is heterozygous for the deletion will show a signal in each of the wells.

VII. Methods of Decreasing ARVC Frequency in a Boxer Dog Population by Selection of ARVC-Free Dogs Also disclosed herein are methods of breeding Boxer dogs that utilize the described ARVC diagnostic methods to decrease the incidence of ARVC in a Boxer dog population. Although ARVC is a familial disease, its symptoms are adult onset. Thus, by the time a dog is determined to have or be predisposed to ARVC, it may have already been used for breeding purposes and therefore it may have already transmitted to the next generation a striatin allele comprising the herein-described eight base pair 3'-UTR deletion.

To prevent such transmission, and thereby decrease the frequency of ARVC in a Boxer dog population, those dogs that a breeder is considering for breeding purposes are screened for ARVC by detecting the defect in the striatin gene (directly or indirectly, for instance by measuring the level of striatin expression) using at least one of the diagnostic methods described herein. In some embodiments the dog breeder has the dogs screened for the presence of the mutation in the striatin 3'-UTR. In other embodiments, the dog breeder will have the dogs screened for a measurable reduction in striatin gene expression. Those dogs that are identified as having (or susceptible to, or carrying the genetic defect for) ARVC can then be removed from the breeding population. In this way, the deletion in the striatin 3'-UTR is not transmitted and the frequency of ARVC is reduced in future generations.

VIII. Screening Methods for Identifying Candidate Compounds to Treat ARVC

Also disclosed herein are methods of screening for candidate compounds that can be used to treat ARVC. As described above, the deletion in the striatin 3'-UTR results in measurably less striatin expression in comparison to control levels. Thus, one of skill in the art will appreciate that compounds that increases striatin RNA (production or stability) or protein expression can be useful for treatment of ARVC or amelioration of its symptom(s).

Compounds that increase striatin expression may be identified by isolating and/or culturing cells from an ARVC-affected or predisposed Boxer dog and contacting a population of the isolated cells with a test compound. Striatin gene expression is measured following the cells being contacted with the test compound, to determine a test level of striatin expression, which level is compared to the level of a control sample (e.g., a sample of cells not contacted with the test compound). Striatin protein or RNA expression is measured by any method, for instance any of the methods described or referred to herein. Any compound that increases striatin expression, stability, or level compared with the control is selected for as a candidate compound that can be useful for ARVC treatment. Such compounds can then be subject to additional examination, testing and development, as will be recognized by one of ordinary skill.

In particular examples, the control is the level of striatin in a population of the isolated cells that were not contacted with the test compound. In other examples, the control is a standard value of striatin expression in at least one ARVC-affected dog cell.

In some embodiments, multiple test compounds may be screened simultaneously by plating cells isolated from the ARVC-affected dog on multiple-welled culture plates. At least one test compounds is then added to each well of the plate and allowed to contact the cells from the ARVC-affected dog.

IX. Kits

This disclosure also provides kits that enable a user to diagnose ARVC in a Boxer dog, including reagents necessary to either detect the presence of the eight base pair mutation in the striatin 3'-UTR or to measure striatin gene expression.

Certain kits can include reagents necessary for DNA sequencing, including, but not limited to primers, DNA polymerase, dNTPs, and ddNTPs.

Other kits can include Taq polymerase and reagents necessary for quantitative real time PCR, including but not limited to, amplification primers, fluorescent label for detection of the amplified template, nucleotides, and buffers necessary to carry out quantitative real time PCR. In further examples, such kits can also contain reverse transcriptase and reagents necessary to reverse transcribe and RNA template in preparation for RT-PCR.

Other kits can include materials necessary for quantitative or qualitative detection of striatin protein, including antibodies that specifically recognize striatin, labeled secondary antibodies that recognize the striatin-specific antibody, and reagents for use in detection of the label on the secondary antibody.

The materials provided in such kits may be provided in any form practicable, such as suspended in an aqueous solution or as a freeze-dried or lyophilized powder, for instance. Kits according to this invention can also include instructions, usually written instructions, to assist the user in carrying out the detection and quantification methods disclosed herein. Such instructions can optionally be provided on a computer readable medium or as a link to an interne page.

The container(s) in which the reagents are supplied can be any conventional container that is capable of holding the supplied form, for instance, microfuge tubes, ampoules, or bottles. In some applications, the reagent mixtures may be provided in pre-measured single use amounts in individual, typically disposable, tubes, microtiter plates, or equivalent containers. The containers may also be compatible with a specific automated liquid handling apparatus.

EXAMPLES

Example 1

Identification of an Association Between a Mutation in the Striatin 3' Untranslated Region and ARVC This example shows the identification of a eight base pair deletion in the striatin 3'-untranslated region of Boxer dogs affected by ARVC.

Figure 3:
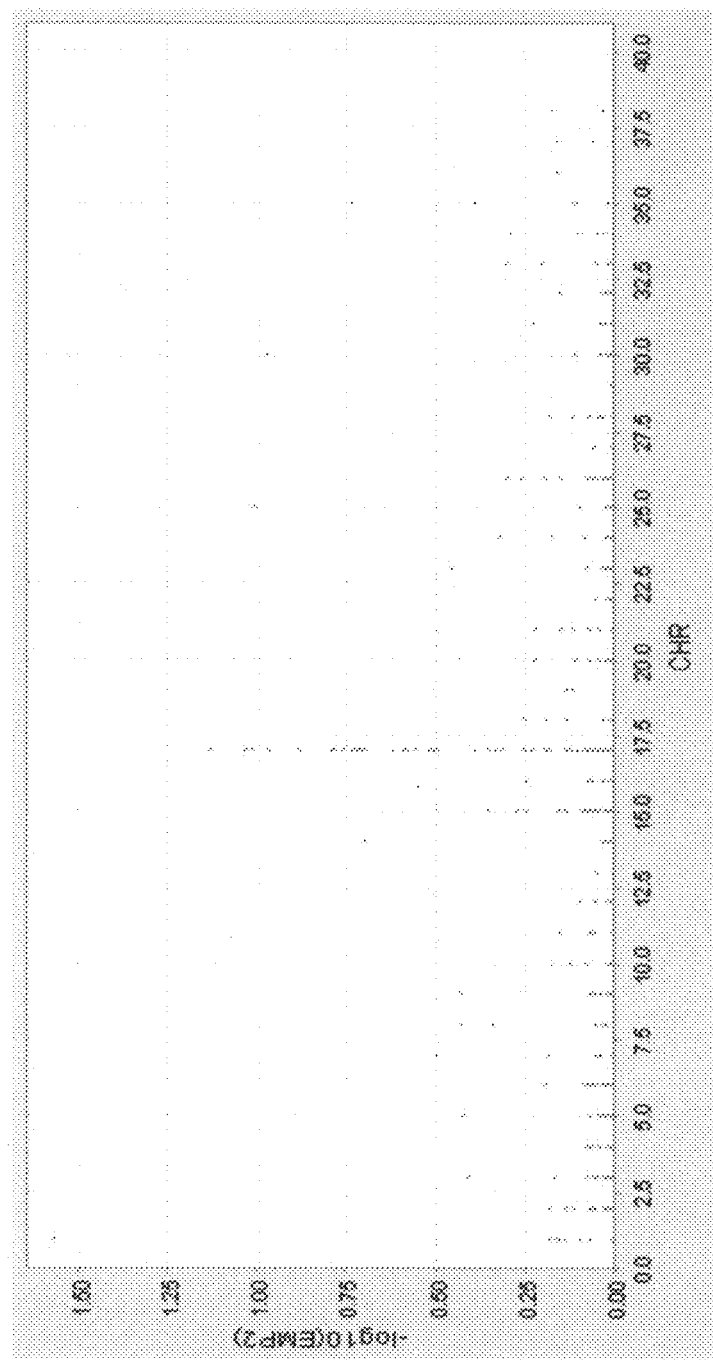
FIG. 3 is a graph showing that a 10 Mb region of genome-wide significant association was identified with the strongest significant loci on chromosome 17 (p genome<0.02).

Boxer dogs over 1 year of age were prospectively recruited for participation in a study to evaluate the clinical aspects of Boxer ARVC. Evaluation included a 24 hour ambulatory electrocardiogram (AECG) using a 3-channel transthoracic system. The monitor tapes were analyzed by a technician using a prospective, user-interaction method under the guidance of a veterinary cardiologist using a Delmar Accuplus 363 Holter analysis system. The total number of VPCs/24 hours was tabulated. An AECG with over 500 VPCs in the absence of other systemic or cardiac disease was considered to be affected. Dogs with less than 100 VPCs/24 hours were considered to be unaffected. DNA samples were collected from unaffected and affected dogs. DNA samples from 48 affected and 48 unaffected dogs were analyzed by association analysis using a Canine Genome SNP Array containing 49,663 SNP markers. SNP genotypes were obtained following the human 500 K array protocol, but with a smaller hybridization volume to allow for the smaller surface area of the canine array (Karlsson et al., Nat Genet, 39:1321-1328, 2007). Case-control GWA mapping was evaluated by using PLINK, followed by the identification of a region of homozygosity in affected individuals based on SNP genotypes (Purcell S, et al., Am J Hum Genet, 81:559-575, 2007). Haplotype analysis was performed with Haploview (Barrett et al., Bioinformatics, 21:263-265, 2005). A 10 Mb region of genome-wide significant association was identified with two significant loci on chromosome 17 (p genome<0.02) (FIG. 3). Fine mapping was performed by selection of SNPs surrounding the identified region of interest in a subset of 20 affected and 20 unaffected dogs and identified an area of significance on chromosome 17 from base pairs 32,256,760-32,388,077 (p=0.003 to 0.009).

Figure 4C:
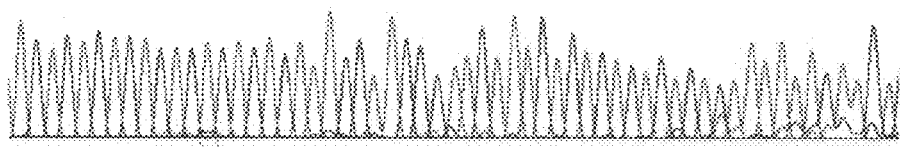

Four genes of possible cardiac importance (Vitrin, Striatin, Fez2, Crim) were identified within or near this region (32, 256,760-32,388,077). Exonic and splice site regions of each of the genes were evaluated with PCR based sequencing using genomic DNA in 5 affected and 2 unaffected dogs. There were no identified differences between the affected and unaffected dogs. Therefore, additional regions of DNA surrounding each gene were examined for areas of high genetic conservation across species since genetic conservation often suggests the presence of important regulatory elements. These areas were also evaluated by PCR based sequencing. This method identified a eight base pair deletion (chr 17:32, 373,918-32,373,925) in a 3' untranslated region of the canine striatin gene in affected ARVC Boxers but not in unaffected Boxers or in 103 unaffected dogs of various breeds (FIGS. 4A-4C; these bases correspond to nucleotides 38-45 in SEQ ID NO: 1). The sequence of chromosome 17, from bases 32,373,881-32,373,945 is: GTGTGTGTGTGTGTGTGTAT-GCATGCGTACATACACA CATACACACACACACACATATATGAAGT (SEQ ID NO: 1). The eight bases that are deleted in the ARVC-affected dogs are underlined and shown in bold. Affected dogs were either homozygous or heterozygous for the deletion. The sequence of this region in Homozygous dogs is shown in FIG. 4C (SEQ ID NO: 2). Homozygous dogs had a statistically greater number of ventricular premature contractions/24 hours and more severe disease than heterozygous dogs (4281 and 1385, respectively) (p<0.05) (FIG. 5).

Evaluation of the genetic region containing the deletion was evaluated for transcriptional importance via CONSITE (online at asp.ii.uib.no:8090/cgi-bin/CONSITE/consite), a genetic computer program that identifies transcription factor binding sites. This evaluation demonstrated that the deletion would remove several binding sites for ZN-Finger and Forkhead transcription factors and would create novel binding sites for other transcription factors. This suggests that the deletion in the striatin 3'-UTR disclosed herein alters transcriptional control of the striatin gene.

Example 2

Striatin Expression is Measurably Lessened in ARVC-Affected Boxer Dogs

This example shows that expression of striatin, a desmosomal protein, is measurably reduced in ARVC-affected Boxer dogs.

I. Methods

RT-PCR: RT-PCR was used to amplify striatin exon 1-containing RNA segments in total RNA extracted from myocardial tissue from ARVC-affected and unaffected dogs with the RNeasy Fibrous Tissue Mini Kit (Qiagen). RT-PCR primers (Forward GCAACAGCGCATTCTCACTTTAG) (SEQ ID No: 3); Reverse GTGGGATGGCTGATGACTCTATTT) (SEQ ID NO: 4)) were designed from the consensus sequence produced from an alignment of the published canine striatin exon 1-containing expressed sequence tags in GenBank (Accession # NW_876263.1; incorporated herein by reference in its entirety as of Apr. 27, 2009). Purified PCR and RT-PCR amplicons were sequenced with an Applied Biosystems 3730×1 DNA analyzer. Amplification of HPRT was used as a control.

Immunofluorescence: Frozen sections (7 µm) on glass coverslips were fixed in acetone at −20° C. for 15 minutes, followed by air-drying for 30 minutes. The sections were rinsed with PBS and blocked with PBS in 2% normal donkey serum, 1% bovine serum albumin and 0.2% Tritonx-100 for 1 hour at room temperature. Sections were incubated with the striatin primary antibody for 1 hour. Sections were then rinsed with PBS and incubated for 30 minutes at room temperature with corresponding secondary donkey antibodies (1:200-1:

500). For double staining, sections were incubated with the actin or PKP-2 primary and the appropriate secondary antibody. DAPI staining was performed to identify the nuclei. After the final rinsing step, sections were mounted with 10% solution of poly vinyl alcohol containing 2.5% 1,4 diazabicyclo-2,2,2-octane (PVA/DABCO Sigma), coverslipped and examined using a confocal microscope (Fidler, *J. Cell and Molec. Med.*, 2008).

Western blot analysis: Frozen myocardial samples from the right ventricle of two non-Boxer controls, two heterozygous Boxer dogs, and two homozygous Boxer dogs were ground to a fine powder while cooled in liquid nitrogen and homogenized in Laemmli buffer. Protein concentration was determined with the Pierce 660 protein assay (Pierce Biotechnology, Rockford, Ill., USA). Twenty micrograms of protein extract for each dog was separated on a 4-20% gradient polyacrylamide gel and transferred to polyvinylidene fluoride (PVDF) membrane. Membranes were blocked with 5% milk and striatin epitopes were probed by both a mouse monoclonal antibody generated against a WD repeat region (also known as the β-transducin or WD-40 repeat) (amino acid 450-600) of striatin (1:100) (BD Transduction Laboratories, Franklin Lakes, N.J., USA) and a rabbit polyclonal antibody against a synthetic striatin peptide which does not cross react with SG2NA (1:300) (Millipore). Blots were stripped and also probed with actin monoclonal antibody (1:100) (BD Transduction Laboratories) as a loading control. The species appropriate secondary IgG-HRP (1:10,000 dilution) (1:3,000) (Santa Cruz Biotechnology Inc, Santa Cruz, Calif., USA) was used followed by chemiluminescence detection and optical density determination using Quantity One software (BioRad, Hercules, Calif., USA). Molecular weight was estimated using a standard curve generated from the Precision Protein Plus Western C standard (BioRad). Data was compared between affected and control animals with a T test. A p<0.05 was considered significant.

II. Results

Figure 6:
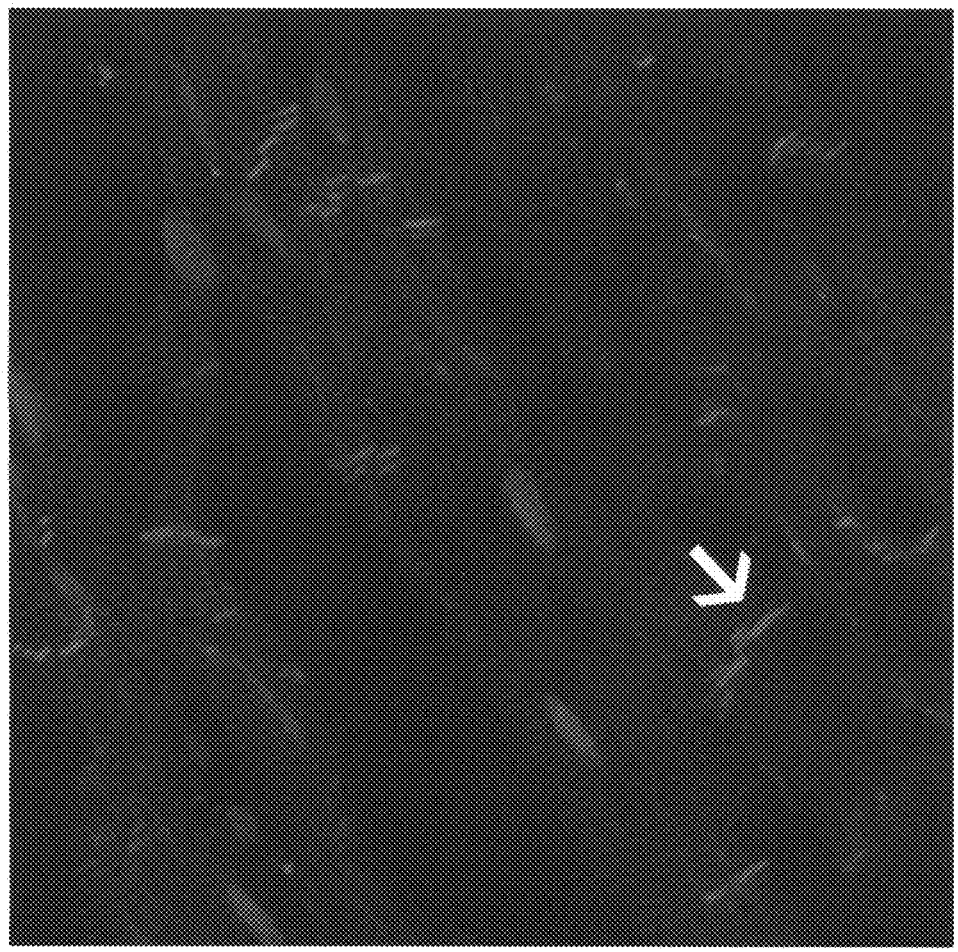
FIG. 6 shows the immunofluorescent labeling of striatin in frozen myocardial tissue from unaffected dogs with a striatin antibody and demonstrates that striatin is a desmosomal protein. Striatin is indicated by bright green color, the white arrow indicates a desmosome.
Figure 7:
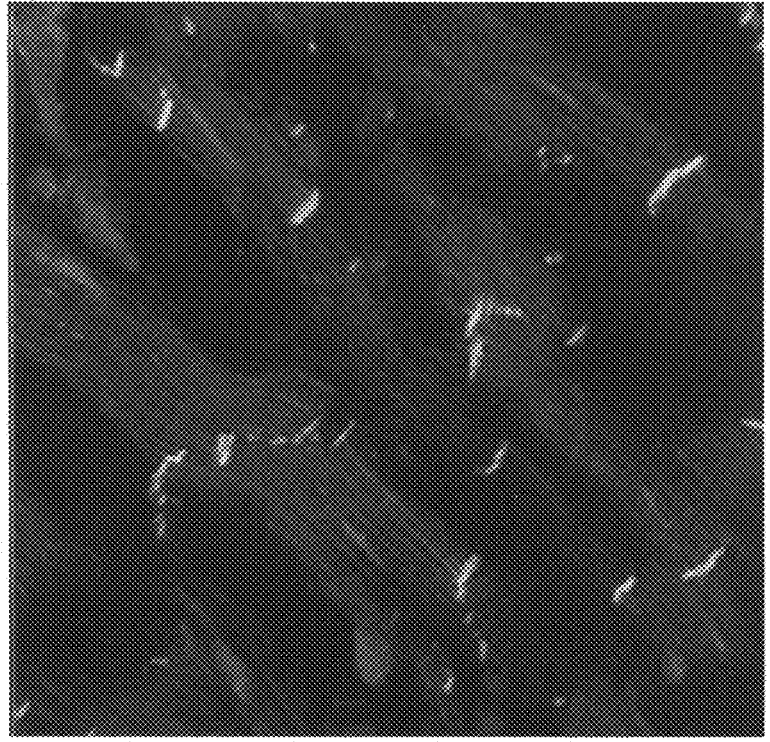
FIG. 7 shows that co-localization of both striatin (green) and plakophilin (red), a known desmosomal protein, demonstrated that the proportion of these two desmosomal proteins was altered in ARVC-affected dogs, confirming the abnormal transcription and production of striatin in ARVC-affected dogs. A) Immunofluorescent labeling of striatin and plakophilin in myocardial tissue from an ARVC-unaffected dog. Note orange (green+red) color of striatin and plakophilin together. B) Immunofluorescent labeling of striatin and plakophilin in myocardial tissue from an ARVC-affected dog. Note yellow color of striatin and plakophilin together. The change in color indicates different proportion of striatin to the other desmosomal protein plakophilin in comparison to normal dog.
Figure 7:
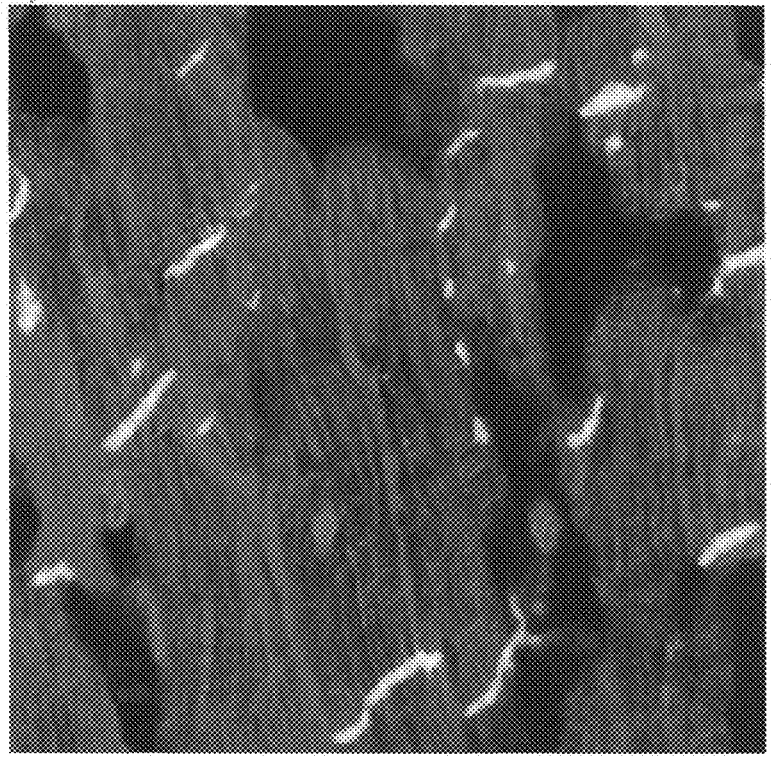

Striatin was not previously known to be expressed in cardiac cells. Therefore, frozen myocardial tissues from dogs unaffected by ARVC was visualized by immunofluorescence using a striatin antibody to determine if striatin is present. As shown in FIG. 6, striatin protein is indeed present in cardiac cells. Additionally, localization of striatin at cell junctions indicated that striatin is in fact a desmosomal (cell junction) protein. That Boxer ARVC results from the mutation of a desmosomal protein is consistent with the existing model of human ARVC, wherein the majority of the disease is caused by a mutation in a gene that encodes for a desmosomal protein. Comparison of co-localization of both striatin and plakophilin (a known desmosomal protein) in myocardial tissue from ARVC-affected and unaffected dogs demonstrated that the proportion of these two desmosomal proteins was altered in ARVC-affected dogs—showing a reduction in striatin expression. However, the expression of plakophilin remained unchanged (FIGS. 7A, and 7B).

Figure 8:
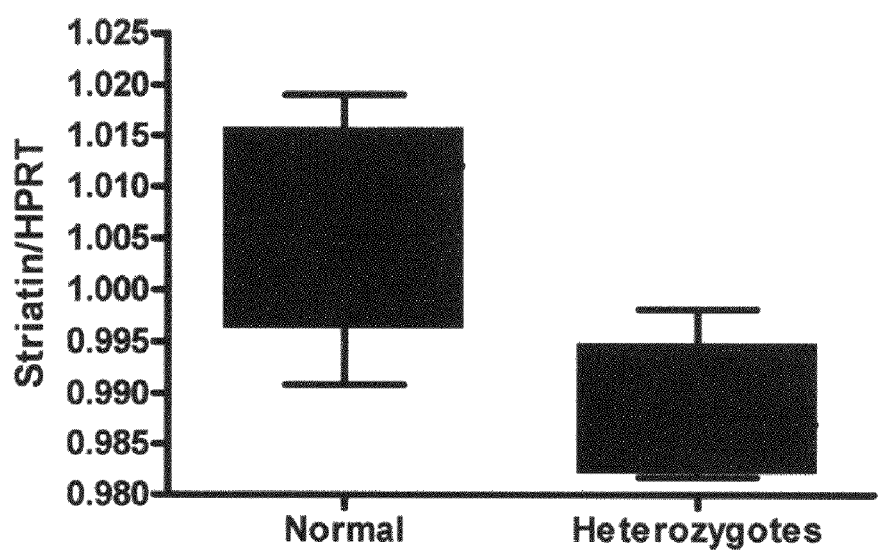
FIG. 8 is a graph showing the measurement of striatin transcript by RT-PCR in myocardial tissue of Boxer dogs. Transcription was compared between ARVC-unaffected dogs and dogs that are heterozygous for the eight base deletion in the striatin 3'-UTR. Quantitation of striatin transcription between dogs was normalized against the housekeeping gene HPRT.
Figure 9:
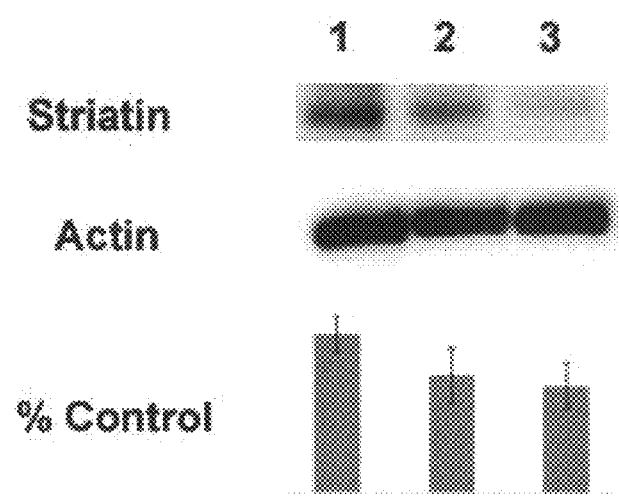
FIG. 9 shows representative results of Western analysis of striatin protein expression in right ventricular myocardial sections. Striatin is shown in the top row; actin loading control is shown in the middle row. Quantification of relative protein levels as a percentage of a non-Boxer canine control for two non-Boxer controls, two heterozygous dogs, and two homozygous ARVC Boxers is shown in the bottom row. Lane 1 is a non-Boxer canine control; lane 2 is a heterozygous ARVC Boxer dog; lane 3 is a homozygous ARVC Boxer dog. Striatin protein as measured by corrected optical density was significantly reduced between the ARVC cases (n=4) and controls (n=2) (p=0.029).

In addition to measurement of striatin expression by immunofluorescence, striatin RNA and protein expression in myocardial tissue was compared between ARVC-affected and control subjects by RT-PCR and Western analysis. As shown in FIG. 8, measurement of striatin RNA by RT-PCR demonstrated that striatin transcription was measurably reduced in ARVC-affected dogs in comparison to unaffected dogs. Western blot detection of striatin protein similarly demonstrated a measurable reduction of striatin protein in comparison to a non-Boxer canine control that expressed striatin at the same level as ARVC-unaffected Boxer dogs (FIG. 9).

Example 3

Methods to Identify ARVC-Affected Boxer Dogs by Detection of Striatin Gene Expression As disclosed herein, reduced striatin expression in comparison to a control is indicative of ARVC in Boxer dogs. Thus, it is possible to identify ARVC-affected dogs by comparison of striatin expression in a subject dog with a known range of expression in dogs that are unaffected by ARVC. As demonstrated in Example 2, the measurable reduction in striatin expression between ARVC-affected and unaffected dogs is observable at both the level transcription and translation. Thus, any method of evaluating striatin gene expression in a subject can be used.

A. Measurement of Striatin Transcription

Striatin transcription can be measured quantitatively in several ways including, but not limited to RT-PCR, quantitative primer extension, quantitative Northern blot, or microarray expression profiling methods. To determine whether there is a measurable reduction in striatin transcription in the subject dog, transcription from one or more dogs known to be unaffected by ARVC will first be determined. Once the range of striatin transcription in one or more dogs unaffected by ARVC is determined, the level of striatin transcription in a subject dog can be determined. The determined amount of striatin transcription will then be compared to that of the dog or dogs known to be unaffected by ARVC. A measurable reduction in striatin transcription in the subject dog as compared to the ARVC-unaffected dog will indicate that the subject dog has ARVC.

B. Detection of Striatin Protein

Striatin expression can also be determined at the level of protein expression. Detection of protein expression can be carried out quantitatively (such as by quantitative western blot) or qualitatively (such as by IF). The expression of striatin protein will first be determined in one or more dogs unaffected by ARVC. Then striatin protein expression will be determined in a subject dog. The detection in the subject dog of a measurable reduction in striatin protein in cardiac cells in comparison to the dog or dogs unaffected by ARVC will indicate that the subject dog is affected by ARVC.

Example 4

Methods to Identify ARVC-Affected Boxer Dogs by Detection of the Eight Base Pair Deletion in the Striatin 3' Untranslated Region This example provides methods for identifying an ARVC-affected dog by detection of the eight base pair deletion in the striatin 3'-untranslated region. To screen a Boxer dog for ARVC, a sample of DNA can be isolated from the dog. To determine whether the dog has a deletion in one or both copies of its striatin gene, a portion of the striatin gene inclusive of chromosome 17 base pairs 32,373,918-32,373,925 (and encompassing nucleotides 38-45 in SEQ ID NO: 1) (or the position that these would occur, if present in the target sequence) can be amplified by PCR or other art-known methods and then sequenced. As shown in FIG. 4, there will be distinctive sequencing patterns found in a dog that has a wild type copy of the striatin gene in comparison to dogs having the eight base pair deletion in one or both copies of the gene. Based on the results of the sequence analysis of the subject dog, tone can diagnose the dog as having ARVC—as the ARVC dog will have 8-base deletion in the 3'-UTR of striatin.

Example 5

Methods of Decreasing ARVC Frequency in a Boxer Dog Population

This example provides a method to decrease the incidence/frequency of ARVC in Boxer dogs through screening and selective breeding. Although ARVC is an inherited disease, its symptoms are adult onset. Thus, symptoms in an ARVC-predisposed dog may not appear until after that dog has been used for breeding and it has already passed on a copy of the striatin gene carrying the eight base pair deletion in its 3'-UTR to the next generation.

To decrease ARVC in a Boxer dog population, candidate breeding dogs are screened by any method for detecting a defect in the striatin gene and thus detecting ARVC, for instance by either a) a measurable reduction in striatin expression or b) the eight base pair deletion in the striatin 3'-UTR. Based on this screen, dogs found to be unaffected by ARVC are deemed suitable for breeding. By breeding only those dogs that are determined to be unaffected by ARVC (that is, dogs that express a normal level of striatin, and/or that do not have a deletion in the 3'-UTR of the striatin gene), the incidence of ARVC in the particular Boxer dog population will be decreased in future generations.

Example 6

Methods of Screening for Compound(s) to Treat an ARVC-Affected Subject

This example provides a method of screening for a candidate compound that can be used to treat ARVC. As described herein, ARVC-affected dogs have measurably less striatin gene expression than unaffected dogs. Thus, compounds that increase striatin expression will be useful for treatment of an ARVC-affected subject, for instance to ameliorate symptoms of ARVC.

An ARVC-affected dog is identified as described herein. A tissue sample is isolated from the dog and a cell culture established. Alternatively a previously-established culture of cells from an ARVC-affected dog is used. In this illustrative example, the cells are divided and plated into eight-chamber cell culture plate(s). A different test compound is added to each of seven of the culture populations, while one of the populations is left untreated as a control. Following sufficient incubation time, the cells are collected, RNA is isolated and striatin expression measured by RT-PCR. The level of striatin RNA in the samples from the test populations is compared to that in the sample from the untreated control population. Alternatively, striatin protein level is tested. Any compound that produces measurably greater striatin expression in a test sample is then selected as a candidate compound for treatment of ARVC.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method of detecting arrhythmogenic right ventricular cardiomyopathy (ARVC) in a Boxer dog subject comprising detecting a defect in the striatin gene in a Boxer dog subject, wherein the defect results in reduced striatin expression, wherein detecting a defect in the striatin gene comprises detecting a deletion of an eight base pair sequence of the 3'-untranslated region (UTR) of the striatin gene, wherein the eight base pair sequence corresponds to nucleotides 38-45 of SEQ ID NO: 1, thereby detecting arrhythmogenic right ventricular cardiomyopathy (ARVC) in the Boxer dog subject.

2. The method of claim 1, wherein detecting the deletion of an eight base pair sequence of the 3'-untranslated region (UTR) of the striatin gene comprises:
   isolating DNA from the Boxer dog subject; and
   sequencing a region of the DNA including the nucleotide sequence corresponding to nucleotides 38-45 of SEQ ID NO: 1.

3. The method of claim 2, further comprising amplifying the region of the DNA including the nucleotide sequence corresponding to nucleotides 38-45 of SEQ ID NO: 1, prior to sequencing the region of the DNA.

4. A method of selectively breeding Boxer dogs to decrease the frequency of arrhythmogenic right ventricular cardiomyopathy (ARVC) in a Boxer dog population comprising: identifying Boxer dogs in a breeding population that have a predisposition to arrhythmogenic right ventricular cardiomyopathy (ARVC) by identifying a defect in the striatin gene, wherein the defect results in aberrant striatin expression;
   selecting for breeding those Boxer dogs that do not have a predisposition to arrhythmogenic right ventricular cardiomyopathy (ARVC); and breeding only selected Boxer dogs, thereby decreasing the frequency of arrhythmogenic right ventricular cardiomyopathy in the Boxer dog population.

5. The method of claim 4, wherein detecting a defect in the striatin gene comprises:
   measuring striatin gene expression in test samples from the dogs in the breeding population; and
   comparing the striatin gene expression in the test samples with a control.

6. The method of claim 5, wherein measuring striatin gene expression comprises measuring striatin RNA in the test samples.

7. The method of claim 5, wherein measuring striatin gene expression comprises measuring striatin protein in the test samples.

8. The method of claim 5, wherein the control is a standard reference value.

9. The method of claim 4, wherein detecting a defect in the striatin gene comprises detecting a deletion of an eight base pair sequence of the 3'-untranslated region (UTR) of the striatin gene, wherein the eight base pair sequence corresponds to nucleotides 38-45 of SEQ ID NO: 1.

10. The method of claim 9, wherein detecting the deletion of an eight base pair sequence of the 3'-untranslated region (UTR) of the striatin gene comprises
    isolating DNA from the dogs of the population; and
    sequencing a region of the DNA including the nucleotide sequence corresponding to nucleotides 38-45 of SEQ ID NO: 1.

11. The method of claim 10, further comprising amplifying the region of the DNA encompassing the nucleotide sequence corresponding to nucleotides 38-45 of SEQ ID NO: 1, prior to sequencing the region of the DNA.

\* \* \* \* \*

UNITED STATES PATENT AND TRADEMARK OFFICE
CERTIFICATE OF CORRECTION

PATENT NO. : 8,334,096 B2  Page 1 of 1
APPLICATION NO. : 12/799574
DATED : December 18, 2012
INVENTOR(S) : Kathryn M. Meurs It is certified that error appears in the above-identified patent and that said Letters Patent is hereby corrected as shown below:

In the Specification:

At column 24, lines 14-17,

" GTGTGTGTGTGTGTGTGTATGCATGCGTACATACACA<u>CATACAC</u>ACACA CACACATATGAAGT (SEQ ID NO: 1)."

should read

-- GTGTGTGTGTGTGTGTGTATGCATGCGTACATACACA<u>CATACACA</u>CACA CACACATATGAAGT (SEQ ID NO: 1).--

Signed and Sealed this
Eighteenth Day of March, 2014

Michelle K. Lee
*Deputy Director of the United States Patent and Trademark Office*